US006399646B1

(12) United States Patent
Riggle

(10) Patent No.: US 6,399,646 B1
(45) Date of Patent: Jun. 4, 2002

(54) TECHNIQUE FOR PREVENTING AND TREATING BACTERIAL WILT BY FOLIAR APPLICATION OF 3-(3-INDOLYL) BUTANOIC ACID

(75) Inventor: Bruce Riggle, Eaton, CO (US)

(73) Assignee: Platte Chemical Company, Greeley, CO (US)

( * ) Notice: Subject to any disclaimer, the term of this patent is extended or adjusted under 35 U.S.C. 154(b) by 0 days.

(21) Appl. No.: 09/823,447

(22) Filed: Mar. 29, 2001

(51) Int. Cl.[7] .................................................. A01N 43/38
(52) U.S. Cl. ......................... 514/416; 514/415; 424/405
(58) Field of Search .......................... 424/405; 514/415, 514/418, 416

(56) References Cited

U.S. PATENT DOCUMENTS 6,015,830 A 1/2000 Matsuda et al.

OTHER PUBLICATIONS

Seymour ed. Spraying, The New Garden Encyclopedia, pp. 1161–1162, 1941.*

"The Role of Auxin In Plant–Disease Development", Tetsuji Yamada, Annu. Rev. Phytopathol. 1993, 31:253–73, Copyright ©1993.

University of Hohenheim, Germany, "Development of new strategies for resistance engineering in transgenic potato towards *Ralstonia* (*Pseudomonas*) *solanacearum* and *Erwinia carotovora*", http://www.uni–hohenheim.de/i3v/00217110/01383041.htm, Jul. 12, 1999.

"Bacterial Wilt—Integrated control of bacterial wilt", Consultant Group on International Agricultural Research, http://www.cgiar.org/CIP/icbw/wilt.htm, Jul. 12, 1999.

Control of the Bacterial Wilt of Tomato Plants by a Derivative of 3–Indolepropionic Acid Based on Selective Actions on *Ralstonia solanacearum*, J. Agric. Food Chem. 1998, 46, 4416–4419, ©1998 American Chemical Society.

* cited by examiner

*Primary Examiner*—Neil S. Levy
(74) *Attorney, Agent, or Firm*—Carol Burton, Esq.; Hogan & Hartson LLP

(57) ABSTRACT

A method of preventing and/or treating plant disease resulting from growth of *Ralstonia Solanacearum* by foliar application to plants of a composition containing 3-IBA. While this 3-IBA composition may contain a racemic mixture of (S) and (R), in the most preferred treatment, the composition contains (S) isomers of 3-IBA. Most preferably, at least two foliar applications are undertaken, spaced apart by more than one day.

5 Claims, No Drawings

TECHNIQUE FOR PREVENTING AND TREATING BACTERIAL WILT BY FOLIAR APPLICATION OF 3-(3-INDOLYL) BUTANOIC ACID

FIELD OF THE INVENTION

The present invention relates to the treatment and prevention of bacterial wilt in plants resulting from Ralstonia Solanacearum infestation. More particularly, the present invention relates to the prevention and treatment of bacterial wilt in crops by treatment with 3-(3-indolyl) butanoic acid.

BACKGROUND OF THE INVENTION

*Ralstonia solanacearum* (hereinafter Ralstonia) is the bacteria responsible for the extremely destructive disease in potatoes, tomatoes, tobacco, eggplant, bell peppers, peanuts and related crops commonly known as bacterial wilt. Bacterial wilt is also known regionally as southern bacterial wilt, brown rot, slime disease and mattery eye. Bacterial wilt is often first observed in plants when one or more leaves droop during the heat of the day. As the disease progresses, all the leaves of the plant may droop. Eventually, the entire plant falls to the ground, its transpiration system choked by milky white bacterial colonies.

Ralstonia, the bacteria responsible for bacterial wilt, is a gram-negative short rod bacteria. The disease progresses as the Ralstonia bacteria plug the vessels of the infected plants—especially the xylem—disrupting the systemic flow of fluids in the plants. This disruption prevents the transport of nutrients throughout the plants and stops the transpiration of water and gases upwards through the plant. As fluids above the blocked areas are transpired away, the structural support of the plants dissipates. The presence of the disease is confirmed by cutting a section of the stem and suspending it in water—if milky white strands are seen oozing from the plant's vascular system into the water, then Ralstonia is likely the source of the disease.

Ralstonia has been characterized as one of the most serious bacterial diseases of potatoes in the warm regions of the world. One of the reasons that worldwide potato production is so vulnerable to bacterial wilt is due to its transmission as a latent infection in seed potatoes. While quarantine measures have been used to avoid spread of the disease by restricting the production of the seed potatoes, this affects the economy in the quarantine regions.

Attempts are also made to control bacterial wilt by crop rotation. This method is not completely satisfactory for a number of reasons. Most problematic is that Ralstonia bacteria may remain in the soil, so that future outbreaks of bacterial wilt cannot be totally avoided by crop rotation alone. In addition, crop rotation can force growers to plant less preferred crops, affecting both public supply of the rotated crop and grower profitability when less desirable crops grown.

Research is currently underway in Europe with the aim of developing a transgenic potato resistant to Ralstonia. However, such a product has not yet been developed, and even if developed, public acceptance of such a product cannot be predicted.

Although the Consultative Group on International Agricultural Research has recently concluded that appropriate chemical control measures that are practical and effective do not exist, U.S. Pat. No. 6,015,830 to MATSUDA, et al., for ANTIBACTERIAL COMPOUNDS FOR RALSTONIA SOLANACEARUM, which issued Jan. 18, 2000, discloses that antibacterial compounds comprising substantially (S)-3-(3-indolyl) butanoic acid can selectively inhibit the growth of Ralstonia. Experiment Part 4 of U.S. Pat. No. 6,015,830 describes the cultivation of Ralstonia bacteria in a physiological brine, in which the extent of Ralstonia colonization is determined by measuring the turbidity of the culture liquid. After an (S)-3-(3-indolyl) butanoic acid solution is added to the culture liquid, turbidity is further measured. An increase in turbidity is treated as indicative of continued Ralstonia growth. The absence of change in turbidity is treated as indicative of suppression of Ralstonia growth. This patent does provide evidence of suppression of Ralstonia growth after the addition of an (S)-3-(3-indolyl) butanoic acid solution. While the patent abstract concludes that bacterial wilt is suppressed dependably, the experiments described in the patent do not describe with any particularity an enabling treatment for growing plants challenged by bacterial wilt.

Experimental use of 3-(3-indolyl) butanoic acid (hereinafter 3-IBA) in hydroponic solutions in which tomato plants are grown is described in "Control of the Bacterial Wilt of Tomato Plants by a Derivative of 3-Indolepropionic Acid Based on Selective Actions on *Ralstonia solanacearum*", by K. Matsuda, et al., *J. Agri. Food Chem.*, 1998, 46, pp. 4416–19. Control of the bacterial growth by 3-IBA in a hydroponic culture of tomato plants is evaluated by first inoculating a hydroponic culture medium with Ralstonia on day 0, adding 3-IBA on day 1, transferring month-old tomato plants to the culture on day 2, and counting the numbers of wilted plants on each day thereafter. The report concludes that in the absence of the 3-IBA, wilt is observed in more than 60% of the plants transferred into hydroponic solutions, while less than 10% of the plants transferred into hydroponic solutions previously treated with 3-IBA are slightly wilted.

While the results reported above are indeed heartening, it is not clear whether the successful suppression of Ralstonia growth in hydroponic solutions prior to tomato plant transfer has direct applicability to soil grown crops. This is because it cannot be ascertained from the information given, whether the 3-IBA effectively suppressed Ralstonia growth prior to the introduction of the tomato plants, so that the hydroponic solution transpired by the transferred tomato plants contained not only well-dispersed Ralstonia bacteria but also an equally well-dispersed concentration of 3-IBA. In the absence of such a ubiquitous medium, it is not known whether plants infected with Ralstonia bacteria, having already lost some transpiration capability, can effectively transport 3-IBA applied to the soil, upward through the partially or wholly plugged xylem, to where Ralstonia bacteria are colonizing.

It is against this background that the significant improvements and advancements of the present invention have taken place.

SUMMARY OF THE INVENTION

A method of preventing and treating bacterial wilt in crops by foliar application of 3-(3-indolyl) butanoic acid is disclosed. Although the preferred optical isomer for inclusion in the compositions of the present invention and foliar application of such compositions, is the (S)-3-(3-indolyl) butanoic acid isomer, use of racemic mixtures of the (S) and (R) isomers are contemplated.

DETAILED DESCRIPTION

A method of preventing and treating bacterial wilt in crops by foliar application of compositions containing 3-(3-indolyl) butanoic acid ("3-IBA") has resulted in the revitalization of severely wilted plants. An exemplary composition is described below in Example I:

EXAMPLE I

The following ingredients were blended:

40.4 g of 3-(3-indolyl) butanoic acid obtained from Kagome Kabushiki Kaisha of Aichi, Japan 0.5 g Morwet EFW (an anionic surfactant available from Witco of Houston, Tex. under product code 147 2841)

g Morwet D425 (an alkylated naphthalen sulfonate, sodium salt-CAS No. 58425-94-5-available from Witco of Houston, Tex., under product code 147 2839)

g Polyfon H (a lignosulfonic acid, sodium salt-CAS No. 8061-51-6-available from Westvaco of Charleston Heights, S.C.)

0.5 g Geropon T-77 (sodium-n-methyl-n-oleoyl taurate-CAS No. 00000137-20-2-available from Rhone-Poulenc, Cranbury, N.J.)

0.05 g Foamaster® Soap L. (a soda soap available from Henkel Corporation, Ambler, Pa.)

4.7 g kaolin clay

The blend was milled to 10 microns, such that 98% of the blend passed a 325 mesh screen. The density of the resulting white product was 25 lbs/ft$^3$ while its specific gravity measured 0.4 g/ml. Suspensions were then made from this product so as to obtain active ingredient concentrations of 0.25 lbs active ingredient per 100 gallons and 2.0 lbs active ingredient per 100 gallons, by mixing water with the product in ratios of 0.185 gram/500 ml and 1.48 gram/500 ml, to create a lower and a higher concentration product. As used herein, the term "active ingredient" refers to 3-IBA. These compositions were then applied to tomato plants by foliar application as describe below in Example II.

EXAMPLE II

One-month old tomato seedlings (Bonny Best™ variety) were transplanted to 4-inch pots and grown for one week after transplanting. Each plant was subjected to a foliar treatment containing a lower concentration of 3-IBA, a higher concentration of 3-IBA, or a control treatment with no 3-IBA, spraying the foliage to run-off. Each treatment consisted of six replications. Plants were treated again seven days later. Two days later, each plant was challenged by inoculation with a suspension containing *Ralstonia solanacearum*. This was accomplished by pouring a 100 ml. bacterial suspension containing $10^8$ CFU/ml. into each 4-inch pot. The roots of the tomato plants were then wounded by piercing the soil three times in each 4-inch pot, thereby creating lesions and increased disease vulnerability. Plants were rated for disease severity on 5 different days. Disease severity ratings were based upon a scale in which 0=healthy, 1=slight wilting, 2=moderate wilting, 3=severe wilting and 4=dead plant. Data obtained are summarized below in Table I and further described in the paragraph which follows.

TABLE 1

| | BACTERIAL WILT SEVERITY | | | | |
|---|---|---|---|---|---|
| Treatment | 9/26/2000 | 9/27/2000 | 9/30/2000 | 10/04/2000 | 10/26/2000 |
| Control | 0.8 | 2.2 | 4.0 | 4.0 | 4.0* |
| foliar application low concentration 3-IBA | 2.5 | 3.0 | 4.0 | 3.8 | 4.0** |
| foliar application higher concentration 3-IBA | 2.3 | 3.0 | 2.8 | 3.3 | 1.5*** |

The 6 control plants (*) inoculated with Ralstonia were all dead by the end of the trial. The 6 plants treated with a low concentration of 3-IBA (**) prior to inoculation were also all dead by the end of the trial.

In contrast, of the 6 plants treated with a higher concentration of 3-IBA (**) prior to inoculation, 3 plants had revived and were recovering at the end of the trial. These 3 plants had been believed close to death at day midway through the trial—and their revival in the weeks which followed was quite unexpected. This result had not been predicted because the nature of the disease—which essentially involves the plugging or choking of plant transpiration systems in the stem. It was expected that treatment of the plant above what would become the center of bacterial colonization—i.e., by foliar application of a bacterial growth suppression compound on leaves distal to the infected stem portions—could effectively contribute to later revival of the subsequently infected plant.

It is noted that in soil grown crops—whose annual numbers worldwide far outweigh the numbers of hydroponic crops—are most easily treated with pesticides and herbicides by post-emergence foliar application. The foliar application techniques of the present invention utilizing compositions containing 3-IBA, thus can easily incorporated into existing crop protection practices.

What is claimed is:

1. A method of preventing and/or treating plant disease resulting from growth of *Ralstonia Solanacearum* by foliar application to plants of a composition containing 3-(3-indolyl) butanoic acid.

2. The method of preventing and/or treating plant disease according to claim 1, wherein the composition contains a racemic mixture of (S) 3-(3-indolyl) butanoic acid and (R) 3-(3-indolyl) butanoic acid.

3. The method of preventing and/or treating plant disease according to claim 1, wherein the composition contains (S) 3-(3-indolyl) butanoic acid isomers.

4. The method of preventing and/or treating plant disease according to claim 1, wherein the 3-(3-indolyl) butanoic acid is foliarly applied with a composition containing an active ingredient concentration of at least 2.0 lbs active ingredient/100 gallons.

5. The method of preventing and/or treating plant disease according to claim 1, wherein the foliar application includes at least two foliar applications spaced apart by more than one day.

* * * * *